(12) United States Patent
Burgess et al.

(10) Patent No.: US 9,421,149 B2
(45) Date of Patent: Aug. 23, 2016

(54) FLUID COLLECTION SYSTEM AND METHODS OF USING SAME

(71) Applicant: Medline Industries, Inc., Mudelein, IL (US)

(72) Inventors: James E. Burgess, Mundelein, IL (US); Kenneth S. Chua, Glenview, IL (US); Joseph B. Dunn, Kansasville, WI (US); Dale F. Greeson, Jr., Palatine, IL (US); Jack E. Maze, Long Grove, IL (US); Alberto C. Savage, Buffalo Grove, IL (US); Arlene A. Siavelis, Northbrook, IL (US); Jennifer E. Tomes, Libertyville, IL (US); Earl D. Wilson, Ingleside, IL (US)

(73) Assignee: Medline Industries, Inc., Mudelein, IL (US)

( * ) Notice: Subject to any disclaimer, the term of this patent is extended or adjusted under 35 U.S.C. 154(b) by 446 days.

(21) Appl. No.: 13/855,399

(22) Filed: Apr. 2, 2013

(65) Prior Publication Data

US 2013/0219682 A1 Aug. 29, 2013

Related U.S. Application Data

(60) Division of application No. 12/266,281, filed on Nov. 6, 2008, now Pat. No. 8,430,855, which is a continuation-in-part of application No. 11/634,714, filed on Dec. 6, 2006, now Pat. No. 7,846,142.

(51) Int. Cl.
*A61G 7/05* (2006.01)
*A61F 5/44* (2006.01)
(Continued)

(52) U.S. Cl.
CPC ............... *A61J 1/1462* (2013.01); *A61F 5/44* (2013.01); *A61G 7/0503* (2013.01); *A61M 1/0019* (2013.01); *A61G 5/10* (2013.01); *Y10T 29/49817* (2015.01); *Y10T 29/49826* (2015.01)

(58) Field of Classification Search
CPC ....... A61F 5/44; A61F 5/4404; A61F 5/4408; A61F 5/453; A61F 5/455; A61G 7/0503; A61G 1/1475; A61J 1/14; A61J 1/1462; A61M 1/0019; A61M 1/0021; Y10T 29/49815; Y10T 29/49817; Y10T 29/49821; Y10T 29/49822; Y10T 29/49824; Y10T 29/49947; Y10T 29/49954; Y10T 29/49963; Y10T 29/49964
USPC ....... 604/317, 320, 332, 343, 346, 347, 349, 604/353–357
See application file for complete search history.

(56) References Cited

U.S. PATENT DOCUMENTS 3,090,968 A 5/1963 Buono
3,220,434 A 11/1965 Garth
(Continued)

FOREIGN PATENT DOCUMENTS

GB 2285086 A * 6/1995 .............. A61M 5/14
WO WO 99/23978 5/1999

OTHER PUBLICATIONS

Written Opinion for International Patent Application No. PCT/US2009/063384, dated Sep. 7, 2010, (4 pages).
(Continued)

*Primary Examiner* — Essama Omgba
(74) *Attorney, Agent, or Firm* — Nixon Peabody LLP (57) ABSTRACT

According to one aspect, a fluid collection bag comprises an inlet opening adapted to receive an inlet tube located on a first side of the fluid collection bag. The fluid collection bag has a length greater than the height. The first side of the fluid collection bag is generally parallel with a length of the fluid collection bag. The fluid collection bag further comprises an outlet opening located on a second side of the fluid collection bag. The fluid collection bag may be reversible such that a first surface or a second opposing surface of the fluid collection bag may face a support element.

12 Claims, 7 Drawing Sheets

(51) Int. Cl.
*B23P 11/00* (2006.01)
*A61J 1/14* (2006.01)
*A61M 1/00* (2006.01)
*A61G 5/10* (2006.01)

(56) References Cited

U.S. PATENT DOCUMENTS

| | | | |
|---|---|---|---|
| 3,237,624 A | | 3/1966 | Jinkens et al. |
| 3,312,221 A | * | 4/1967 | Overment .................. 604/317 |
| 3,345,023 A | | 10/1967 | Scott et al. |
| 3,529,598 A | | 9/1970 | Waldman et al. |
| 3,534,738 A | | 10/1970 | Huck |
| 3,537,109 A | | 11/1970 | Spurrier et al. |
| 3,537,455 A | * | 11/1970 | Waldman et al. ............ 604/323 |
| 3,537,456 A | * | 11/1970 | Harautuneian et al. ...... 604/326 |
| 3,564,620 A | * | 2/1971 | Clark .......................... 4/144.1 |
| 3,592,343 A | | 7/1971 | Swett et al. |
| 3,699,964 A | * | 10/1972 | Ericson ......................... 604/33 |
| 3,963,154 A | * | 6/1976 | Schwartz ............... A47G 25/32 223/85 |
| 3,965,900 A | | 6/1976 | Boedecker |
| 4,015,605 A | | 4/1977 | McWhorter |
| 4,019,707 A | | 4/1977 | Quinn et al. |
| 4,027,842 A | | 6/1977 | Mittleman |
| 4,051,578 A | | 10/1977 | Manschot et al. |
| 4,074,838 A | * | 2/1978 | Blasnik ................ A47G 25/32 223/85 |
| 4,188,989 A | | 2/1980 | Andersen |
| 4,219,177 A | | 8/1980 | O'Day |
| 4,254,771 A | * | 3/1981 | Vidal .......................... 604/325 |
| 4,305,405 A | | 12/1981 | Meisch |
| 4,312,352 A | | 1/1982 | Meisch et al. |
| 4,317,550 A | | 3/1982 | Hannah |
| 4,343,316 A | * | 8/1982 | Jespersen ..................... 600/584 |
| 4,393,880 A | | 7/1983 | Taylor |
| 4,417,892 A | | 11/1983 | Meisch |
| 4,501,584 A | | 2/1985 | Cianci et al. |
| 4,559,937 A | | 12/1985 | Vinson |
| 4,562,984 A | | 1/1986 | Sherlock et al. |
| 4,650,478 A | | 3/1987 | Dunn |
| 4,723,950 A | | 2/1988 | Lee |
| 4,772,278 A | | 9/1988 | Baber |
| 4,857,042 A | | 8/1989 | Schneider |
| 4,886,510 A | | 12/1989 | Matsuura |
| 4,893,587 A | | 1/1990 | Bailey, Jr. |
| 4,936,837 A | | 6/1990 | Wexler et al. |
| 5,009,236 A | | 4/1991 | Brothers |
| 5,119,675 A | | 6/1992 | Mohiuddin |
| 5,148,940 A | | 9/1992 | Mendise |
| 5,217,443 A | | 6/1993 | Oxley |
| 5,267,989 A | | 12/1993 | Moyet-Ortiz |
| 5,356,398 A | | 10/1994 | Willis |
| 5,375,799 A | | 12/1994 | Rhodes |
| 5,429,624 A | | 7/1995 | Coelho, Jr. |
| 5,647,670 A | | 7/1997 | Iscovich |
| 5,792,127 A | | 8/1998 | Marran |
| 5,842,233 A | | 12/1998 | Brodén |
| 5,911,786 A | | 6/1999 | Nielsen et al. |
| 5,935,115 A | | 8/1999 | Espina |
| 5,967,200 A | | 10/1999 | Hall |
| 6,007,521 A | | 12/1999 | Bidwell et al. |
| 6,098,210 A | | 8/2000 | Broden |
| 6,132,407 A | | 10/2000 | Genese et al. |
| 6,212,698 B1 | | 4/2001 | Stingley et al. |
| 6,318,419 B1 | | 11/2001 | Lee |
| 6,471,680 B1 | | 10/2002 | Cawood |
| 6,482,190 B1 | | 11/2002 | Genese et al. |
| 6,491,673 B1 | | 12/2002 | Palumbo et al. |
| 6,543,064 B1 | | 4/2003 | Prall et al. |
| 6,709,420 B1 | * | 3/2004 | Lincoln et al. ............... 604/323 |
| 6,716,200 B2 | | 4/2004 | Bracken et al. |
| 6,736,803 B2 | | 5/2004 | Cawood |
| 6,796,974 B2 | | 9/2004 | Palumbo et al. |
| 6,857,137 B2 | | 2/2005 | Otto |
| 6,858,021 B2 | | 2/2005 | Washington |
| 6,887,230 B2 | | 5/2005 | Kubalak et al. |
| 6,904,621 B2 | | 6/2005 | Otto et al. |
| 7,001,370 B2 | | 2/2006 | Kubalak et al. |
| 7,008,407 B1 | | 3/2006 | Kamp |
| 7,846,142 B2 | * | 12/2010 | Burgess .................... A61F 5/44 604/317 |
| 8,361,044 B2 | * | 1/2013 | Marshall ....................... 604/327 |
| 8,430,855 B2 | * | 4/2013 | Burgess et al. .............. 604/317 |
| 8,790,320 B2 | * | 7/2014 | Christensen ................. 604/318 |
| 2007/0203463 A1 | | 8/2007 | Salvadori et al. |
| 2007/0203495 A1 | | 8/2007 | Green et al. |
| 2008/0140033 A1 | | 6/2008 | Burgess et al. |
| 2009/0024099 A1 | | 1/2009 | Burgess et al. |
| 2009/0062755 A1 | * | 3/2009 | Burgess et al. .............. 604/326 |
| 2009/0234310 A1 | * | 9/2009 | Marshall ....................... 604/327 |
| 2013/0219682 A1 | * | 8/2013 | Burgess et al. .............. 29/426.2 |

OTHER PUBLICATIONS

Search Report for International Patent Application No. PCT/US2009/063384, dated Sep. 7, 2010, (5 pages).

* cited by examiner

FLUID COLLECTION SYSTEM AND METHODS OF USING SAME

CROSS-REFERENCE TO RELATED APPLICATION

This application is a divisional of U.S. application Ser. No. 12/266,281, filed Nov. 6, 2008, now issued as U.S. Pat. No. 8,430,855, which is a continuation-in-part of U.S. application Ser. No. 11/634,714, filed Dec. 6, 2006, now issued as U.S. Pat. No. 7,846,142, each of which is hereby incorporated by reference in its entirety.

FIELD OF THE INVENTION

This invention relates to the collecting and measuring of body fluid. More specifically, the present invention is directed to a sanitary fluid collection system and methods of using such a system.

BACKGROUND OF THE INVENTION

Fluid collection systems are typically used in hospitals to monitor the discharge of urine, blood, or exudate from bedridden patients. Such fluid collection systems include a fluid collection bag. The catheter is typically connected to the fluid collection bag and is generally suspended at a patient's bedside. Fluid collection bags generally have an inlet tube near the uppermost portion of the bag where the urine enters and an outlet near the bottom portion of the fluid collection bag, which permits discharge of the urine.

Medical beds that raise and lower are commonly used in healthcare facilities. Placing medical beds in a low position is recommended for patient safety. Having medical beds in a low position makes it easier to tend to patients and provides for a shorter fall should a patient fall from the bed. However, many fluid collection bags rest on the floor when medical beds are in their low position. Since the outlet is typically located at the bottom portion of fluid collection bags, there exists the potential for contamination and the spread of bacteria when fluid collection bags are permitted to rest on the floor.

Accordingly, there exists a need to provide a fluid collection system having a fluid collection bag that is adapted to suspend from a medical bed in a low position without contacting the floor. It would, thus, be desirable to have a fluid collection system having a fluid collection bag that addresses this need.

BRIEF DESCRIPTION OF THE DRAWINGS

The foregoing and other advantages of the invention will become apparent upon reading the following detailed description and upon reference to the drawings.

While this invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

The phrases "fluid collection bag" and "fluid collection system" are used throughout the description and will, thus, be defined for clarity purposes. A "fluid collection bag" is a receptacle for collecting bodily fluid, such as urine, blood, and exudate. A "fluid collection system" includes a receptacle, tubing, connectors, and mechanical supports and may include a means to prevent the backflow of fluid.

Figure 1:
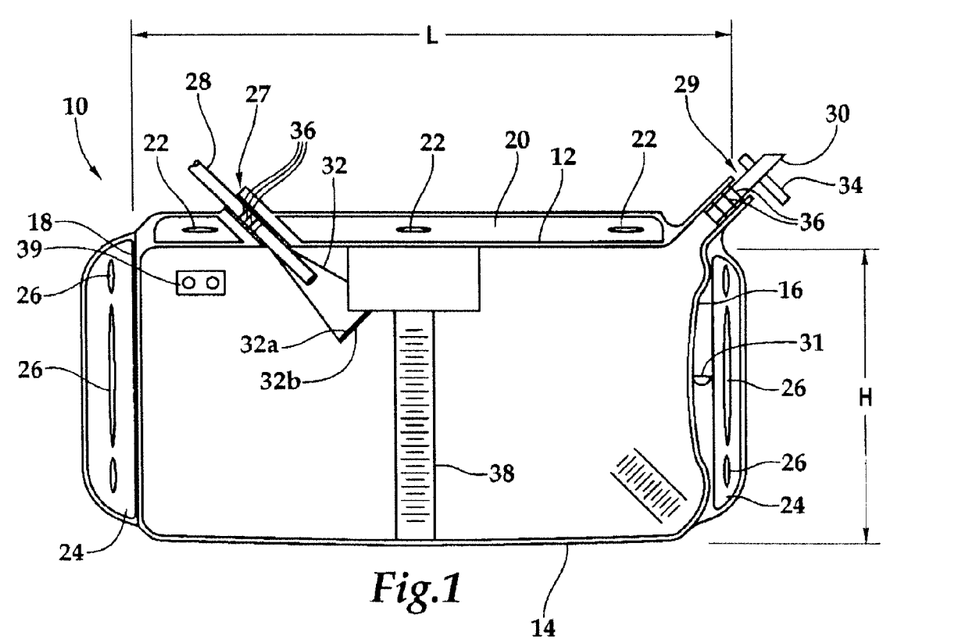
FIG. 1 illustrates a fluid collection bag according to one embodiment.

Referring initially to FIG. 1, a fluid collection bag 10 adapted for use in a fluid collection system 70 (shown in FIG. 3) is illustrated. The fluid collection bag 10 is generally comprised of plastic. However, the fluid collection bag 10 may be comprised of any impervious flexible, rigid or semi-rigid material. The fluid collection bag 10 has a first side 12 and a second side 14 along a length L of the fluid collection bag 10. The fluid collection bag 10 further includes a first end 16 and a second end 18 along a height H of the fluid collection bag 10. The length L of the fluid collection bag 10 is generally greater than the height H of the fluid collection bag 10. In other words, the fluid collection bag 10 has a longitudinal axis LA (illustrated in FIG. 3) aligned with the length L of the fluid collection bag 10. In one embodiment, the length L of the fluid collection bag 10 is approximately twice as long as the height H of the fluid collection bag 10. In other embodiments, the fluid collection bag 10 may have a length L ranging from about 1.5 to about 5 times the height H of the fluid collection bag 10. However, other dimensional proportions are contemplated and may be used in accordance with one or more embodiments of the present invention. Despite the potential variation in length and height proportions, an elongated length and a shorter height assist in enabling the fluid collection bag 10 to hang on a bed frame and not contact the ground when the bed is in a low position. Thus, the elongated length and shorter height assist in inhibiting the potential for contamination and/or spread of infection. While the fluid collection bag 10 is shown having a generally rectangular shape, the fluid collection bag 10 may take other polygonal and non-polygonal forms.

The first side 12 includes a side reinforcement 20 having one or more side openings 22. The side reinforcement 20 and side openings 22 are adapted to enable the fluid collection bag 10 to be attached to a mounting bracket 50 (see FIG. 2) or other mounting device, as will be described below. Although three side openings 22 are depicted in the embodiment of FIG. 1, any number of side openings 22 suitable for assisting in mounting or otherwise affixing the fluid collection bag 10 onto a mounting bracket 50 or other mounting device may be used. The side reinforcement 20 is generally comprised of plastic. However, other materials may be used for the side reinforcement 20, such as woven or non-woven material, molded or stamped material, wood, metal, paperboard, or any rigid or flexible material. The side openings 22 may be generally elliptically-shaped and should be of a size sufficient to facilitate affixing, mounting, hanging or manipulating the fluid collection bag 10. The side openings 22 may take other shapes than those depicted in the FIGS. The side openings 22 are generally reinforced for ease of use and durability.

The first end 16 and the second end 18 include end reinforcements 24 having one or more end openings 26. The end openings 26 assist in enabling the fluid collection bag 10 to be handled by a nurse or other handler of the fluid collection bag 10. Additionally, the end openings 26 assist in permitting the fluid collection bag 10 to become associated with and/or affixed to other types of objects (see, e.g., FIG. 4). By providing one or more side openings 22 and one or more end openings 26 at different locations on the fluid collection bag 10, the fluid collection bag 10 may be secured to various types of objects including, but not limited to, a bed such as a medical bed, patient aids such as a pole, a chair, a wheelchair, a walker, and a person. The end reinforcements 24 are generally comprised of plastic but can be comprised of woven or non-woven material, molded or stamped material, wood, metal, paperboard, or any rigid or flexible material, as well. The end openings 26 may be generally elliptically-shaped, but may also take other shapes. Furthermore, the end openings 26 are of a size sufficient to facilitate affixing, mounting, hanging or manipulating the fluid collection bag 10. The end openings 26 are generally reinforced for ease of use and durability. Although a total of six end openings 26 are depicted in the embodiment of FIG. 1, any number of end openings 26 suitable for assisting in affixing, mounting, hanging or manipulating the fluid collection bag 10 onto an object may be used. It should be noted that the side openings 22 on the side reinforcements 20 and the end openings 26 on the end reinforcements 24 are generally symmetrical, thereby enabling the fluid collection bag 10 to be affixed, mounted, hung or manipulated to any side of a bed or other object.

An inlet opening 27, adapted to receive an inlet tube 28, and an outlet opening 29 having an outlet tube 30, are located along the first side 12 of the fluid collection bag 10. However, it is contemplated that the fluid collection bag 10 may have additional inlet and outlet openings and tubes. Additionally, the inlet and outlet openings 27, 29 may be located in other positions on the fluid collection bag 10 than those illustrated in the FIGS. Before use of the fluid collection bag 10, the inlet tube 28 is associated with the fluid collection bag 10 at the inlet opening 27 at one end. The exposed end of the inlet tube 28 is typically connected to a catheter (not illustrated). The outlet tube 30 is associated with the fluid collection bag 10 at the outlet opening 29 at one end. The exposed end of the outlet tube 30 may be inserted into a drain tube holder 31.

In the illustrated embodiment, the inlet tube 28 associates with the fluid collection bag 10 at an angle to reduce twisting and to allow for good drainage. In one embodiment, the inlet tube 28 may associate with the fluid collection bag 10 at an angle within the range of about 30° to about 50°. However, it is contemplated that any angle which is suitable for reducing twisting and allowing good drainage for the inlet tube 28 may be used.

Near the inlet opening 27 and internal to the fluid collection bag 10 is an anti-reflux mechanism 32. The anti-reflux mechanism 32 is adapted to generally surround the inlet tube 28 and comprises two sheets 32a, 32b having different lengths in the embodiment shown in FIG. 1. The anti-reflux mechanism 32 may be comprised of vinyl; however, other materials are contemplated for use. Some non-limiting examples of materials for use in the anti-reflux mechanism 32 include plastic film, molded plastic, and rubber. At one end, at least one sheet, i.e., 32a or 32b, of the anti-reflux mechanism 32 may be associated with the fluid collection bag 10 at or near the inlet opening 27 or the inlet tube 28 itself. The other end of the anti-reflux mechanism 32 is free. The anti-reflux mechanism 32 assists in allowing fluid to enter the fluid collection bag 10 while inhibiting fluid from exiting the fluid collection bag 10 through the inlet tube 28. To inhibit fluid from exiting through the inlet tube 28, the sheets 32a, 32b collapse and assist in sealing the end of the inlet tube 28 internal to the fluid collection bag 10 when fluid attempts to exit through the inlet tube 28. It should be noted that other types of anti-reflux mechanisms having different designs and/or different numbers of sheets may also be used.

A user may control the exit of fluid from the fluid collection bag 10 through the outlet tube 30 using a valve 34. The valve 34 may be any of those types of valves adapted to open or close a fluid path to allow fluid to drain or keep fluid from draining. In one embodiment, the valve 34 is adapted to replace a drainage hole with a post when activated. In other embodiments, the valve 34 may, for example, be a twist valve, a tube that closes with a mechanical compression against it, or a roller clamp. Additionally, in some embodiments, more than one valve may be utilized.

The inlet tube 28 and the outlet tube 30 may include one or more ribs 36 to discourage kinking or compression within the inlet and outlet tubes 28, 30. The ribs 36 enable good flow through the inlet and outlet tubes 28, 30 and allow for good drainage of the fluid collection bag 10. The fluid collection bag 10 may also include a vent 39 and a printed window 38. The vent 39 is a hydrophilic air vent allowing air transfer to inhibit pressure effects such as a vacuum effect in the fluid collection bag 10. The printed window 38 has measurement line(s) to enable easy urine volume output determination.

Figure 2:
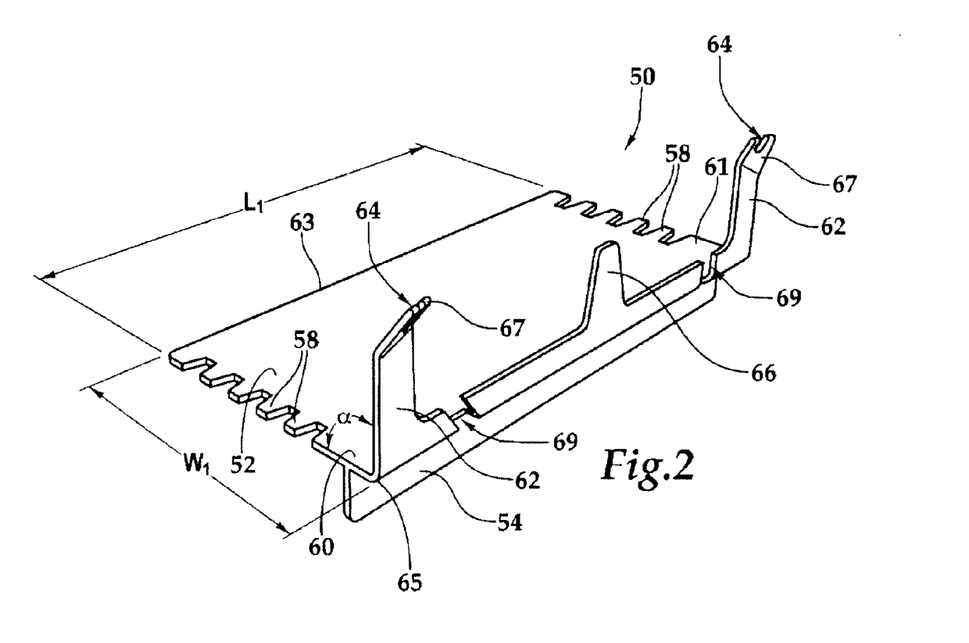
FIG. 2 illustrates a mounting bracket adapted for use with the fluid collection bag of FIG. 1.

Referring now to FIG. 2, the mounting bracket 50 is illustrated according to one embodiment of the present concepts. The mounting bracket 50 is generally comprised of a rigid material for stability. Some non-limiting materials that may be used for the mounting bracket 50 include plastic, wood, metal, or paper board. The mounting bracket 50 may include a base 52 and optionally one or more support members 54. The base 52 has a first end 60 and a second end 61 along a base width $W_1$ of the mounting bracket 50. The base 52 further includes a first side 65 and a second side 63 along a base length L₁ of the mounting bracket 50. The base width W₁ may be about one-half of an inch (about 1.27 centimeters) or more. In one embodiment, the base width W₁ is about six inches (about 15.24 centimeters). In one embodiment, the base length L₁ is about ten inches (about 25.4 centimeters). However, other sizes are also contemplated and the base length L₁ may be any length sufficient to support the fluid collection bag 10. The support member 54 extends from the base 52 at about the first side 65 of the base 52 in a generally perpendicular direction opposite to attachment members 62. While the mounting bracket 50 is depicted in FIG. 2 as having a generally rectangular shape, it is contemplated that other shapes may be used. It is contemplated that the mounting bracket 50 may take on any configuration or size that is suitable for mounting or otherwise affixing the fluid collection bag 10 onto a bed frame or other desired object.

Generally, the mounting bracket 50 is adapted to removably associate with an object, such as a bed for example. More specifically, the base 52 and the support member 54 of the mounting bracket 50 are adapted to contact an end of a bed frame, wherein the base 52 rests on top of the bed frame and the support member 54 may contact the side of the bed frame (see, e.g., FIG. 3). Although a generally rectangular shape is shown, the shape of the base 52 and support member 54 may vary to enable a removable attachment to different types of objects and different desired end uses. Furthermore, the mounting bracket 50 may include components other than or in addition to the base 52 and support member 54 to associate with desired objects. To enhance the attachment of the mounting bracket 50 to certain objects, the base 52 may include one or more securement tabs 58 located along the first end 60 and/or the second end 61 of the base 52. The securement tabs 58 will be described in further detail below.

As mentioned above, the fluid collection bag 10 is adapted to associate with a mounting bracket such as the mounting bracket 50 depicted in FIG. 2 or with any other mounting device. The mounting bracket 50 may include one or more attachment members 62 adapted to associate with the one or more side openings 22 of the fluid collection bag 10. Although the mounting bracket 50 is shown with two attachment members in FIG. 2, any number of attachment member(s) suitable for mounting or otherwise affixing the mounting bracket 50 or other mounting device to the fluid collection bag 10 may be used. The attachment members 62 form an angle α with the base 52 of the mounting bracket 50. In some embodiments, such as that shown in FIG. 2, the angle α is about ninety-degrees (about 90°). In other embodiments, the angle α may be greater than 90° (i.e., an obtuse angle). Having an angle α greater than 90° allows the fluid collection bag 10 to hang away from the bed and allow room for fluid to expand the fluid collection bag 10. In some embodiments, the angle α is between about 90° and about 110°.

The attachment members 62 may include a top portion 67 having an inlet tube guide 64. The inlet tube guide 64 on the top portion 67 is adapted to receive and hold the inlet tube 28 in place when the fluid collection bag 10 is associated with the mounting bracket 50. The top portion 67 is angled and assists in providing good placement of the inlet tube 28 for good drainage. In the embodiment depicted in FIG. 2, the inlet tube guide 64 is provided on both attachment members 62 because the mounting bracket 50 is "reversible" and may be used on either side of a bed or object. However, in other embodiments, only one of the attachment members 62 may include an inlet tube guide 64. The mounting bracket 50 may optionally include one or more center attachment members 66 to provide additional support for the fluid collection bag 10. The center attachment member 66 may be adapted to associate with one or more side openings 22 of the fluid collection bag 10.

In some embodiments, the mounting bracket 50 may include one or more cut-out portions 69 adapted to receive the inlet opening 27 and inlet tube 28 of the fluid collection bag 10 to facilitate flush mounting of the fluid collection bag 10. The mounting bracket 50 is not limited to comprising one continuous piece. To facilitate storage, shipping, and handling of the mounting bracket 50, the mounting bracket 50 may comprise a plurality of pieces adapted for assembly.

Figures 3, 4:
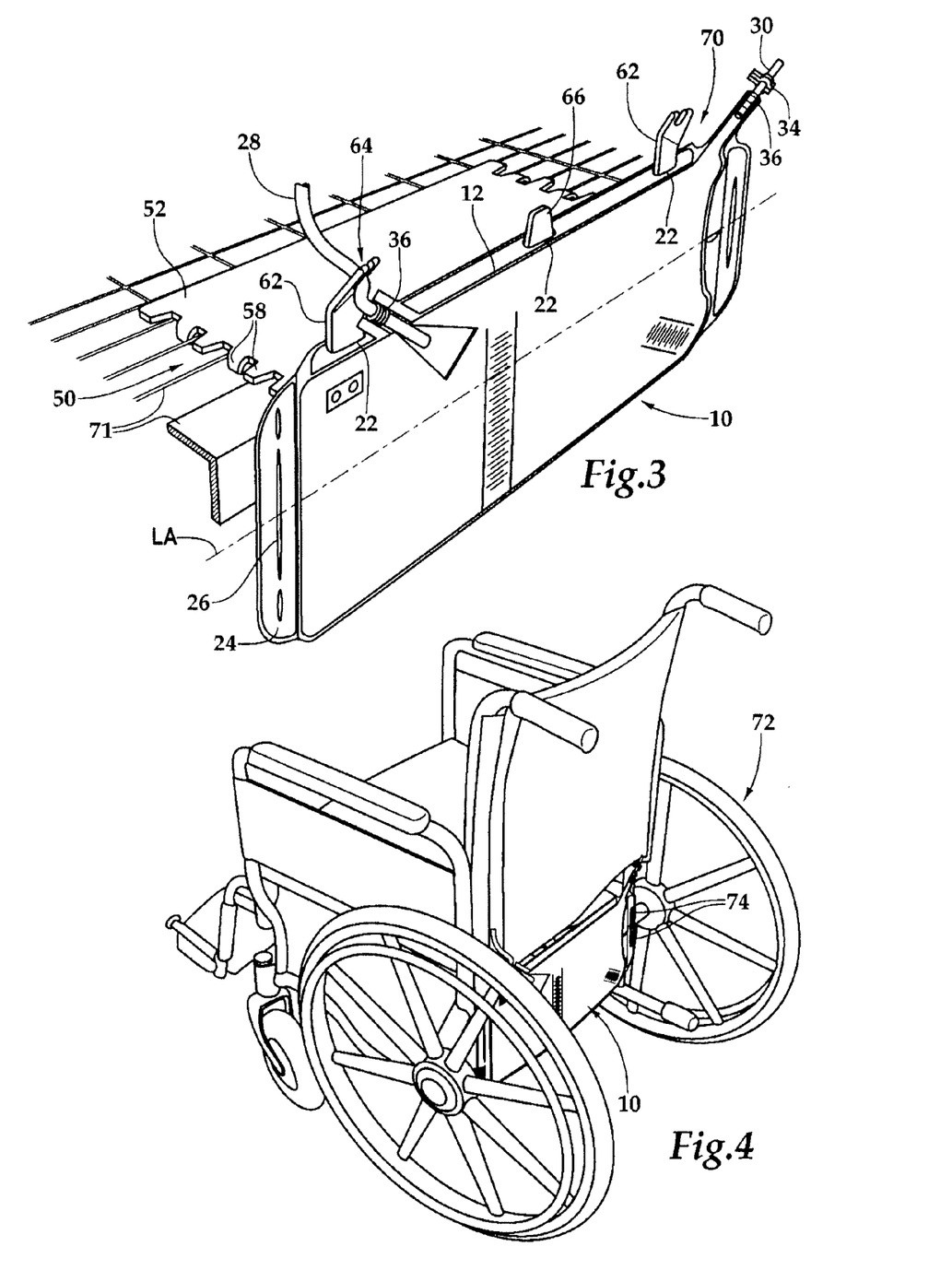
FIG. 3 shows a fluid collection system according to one embodiment shown associated with a bed frame.
FIG. 4 shows the fluid collection bag according to one embodiment shown associated with a wheelchair.

Referring now to FIG. 3, the fluid collection system 70, including the fluid collection bag 10 and the mounting bracket 50, are illustrated in use. The base 52 and support member 54 (not visible) of the mounting bracket 50 contact a bed frame 71. The side openings 22 of the fluid collection bag 10 have been placed over the attachment members 62 and center attachment member 66 to provide a removable attachment between the fluid collection bag 10 and the mounting bracket 50. The securement tabs 58 have been bent by a user around portions of the bed frame 71 to further secure the mounting bracket 50 to the bed frame 71. The inlet tube guide 64 maintains the inlet tube 28 in an optimal position for fluid flow through the inlet tube 28.

As illustrated, the longitudinal axis LA of the fluid collection bag 10 is oriented substantially parallel to the ground. Having the outlet tube 30 associated with the fluid collection bag 10 at or near the first side 12 of the fluid collection bag 10 keeps the outlet tube 30 away from the ground. By having the outlet tube 30 associated with the fluid collection bag 10 at or near the first side 12 of the fluid collection bag 10 and by keeping the collection bag 10 away from the ground, the risk for contamination and/or spread of infection when a bed is in a low position is reduced.

As mentioned above, the end openings 26 on the end reinforcements 24 are provided to enable attachment of the fluid collection bag 10 to objects in addition to beds. Such additional objects include, but are not limited to, patient aids such as a pole, a chair, a wheelchair, a walker, and person. Referring now to FIG. 4, the fluid collection bag 10 is shown associated with a wheelchair 72. As shown in FIG. 4, one or more pieces of securement material tape 74 may be used instead of or in addition to the mounting bracket 50 to affix the fluid collection bag 10 to a wheelchair or other objects. In one embodiment, the securement material 74 is Velcro® or other hook and loop type fastening devices. In other embodiments, the securement material for affixing, mounting, hanging or otherwise manipulating the fluid collection bag 10 onto the desired object may include snaps, cords, buttons, or other fastening devices.

To use the fluid collection system 70, a user would associate the mounting bracket 50 with an object, such as a bed frame, as illustrated in FIG. 3. The user would then orient the longitudinal axis LA of the fluid collection bag 10 substantially parallel to the ground and removably associate the fluid collection bag 10 with at least one attachment member 62 or 66 of the mounting bracket 50. As illustrated in FIG. 3, the side openings 22 may be utilized to associate the fluid collection bag with the attachment members 62 and 66.

Figure 5:
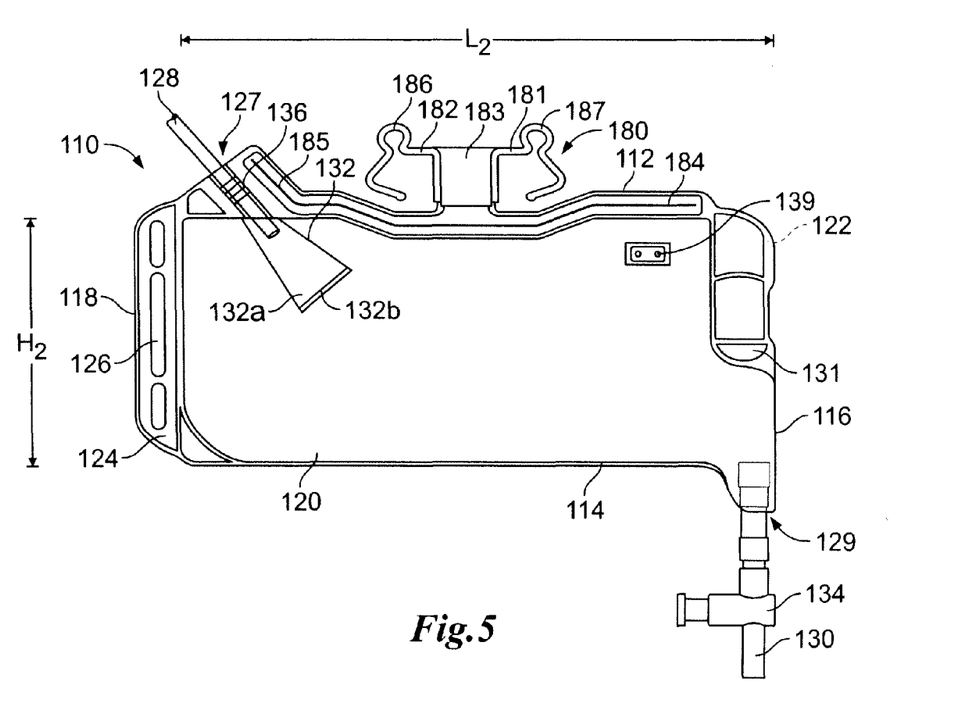
FIGS. 5-6 show a fluid collection bag according to a further embodiment.

Referring now to FIG. 5, a fluid collection bag 110 is illustrated. As with the embodiment described above in FIG. 1, the fluid collection bag 110 is generally comprised of plastic. However, the fluid collection bag 110 may be comprised of any impervious flexible, rigid or semi-rigid material. The fluid collection bag 110 has a first side 112 and a second side 114 along a length $L_2$ of the fluid collection bag 110. The fluid collection bag 110 further includes a first end 116 and a second end 118 along a height $H_2$ of the fluid collection bag 110. The length $L_2$ of the fluid collection bag 110 is generally greater than the height $H_2$ of the fluid collection bag 110. In one embodiment, the length $L_2$ of the fluid collection bag 110 is approximately twice as long as the height $H_2$ of the fluid collection bag 110. In other embodiments, the fluid collection bag 110 may have a length $L_2$ ranging from about 1.5 to about 5 times the height $H_2$ of the fluid collection bag 110. However, other dimensional proportions are contemplated and may be used in accordance with one or more embodiments of the present invention. Despite the potential variation in length and height proportions, an elongated length and a shorter height assist in enabling the fluid collection bag 110 to hang on a bed frame and not contact the ground when the bed is in a low position. Thus, the elongated length and shorter height assist in inhibiting the potential for contamination and/or spread of infection. Such a configuration also allows for easier draining of the fluid collection bag 110 as the fluid collection bag 110 is a farther distance from the floor.

Figure 7:
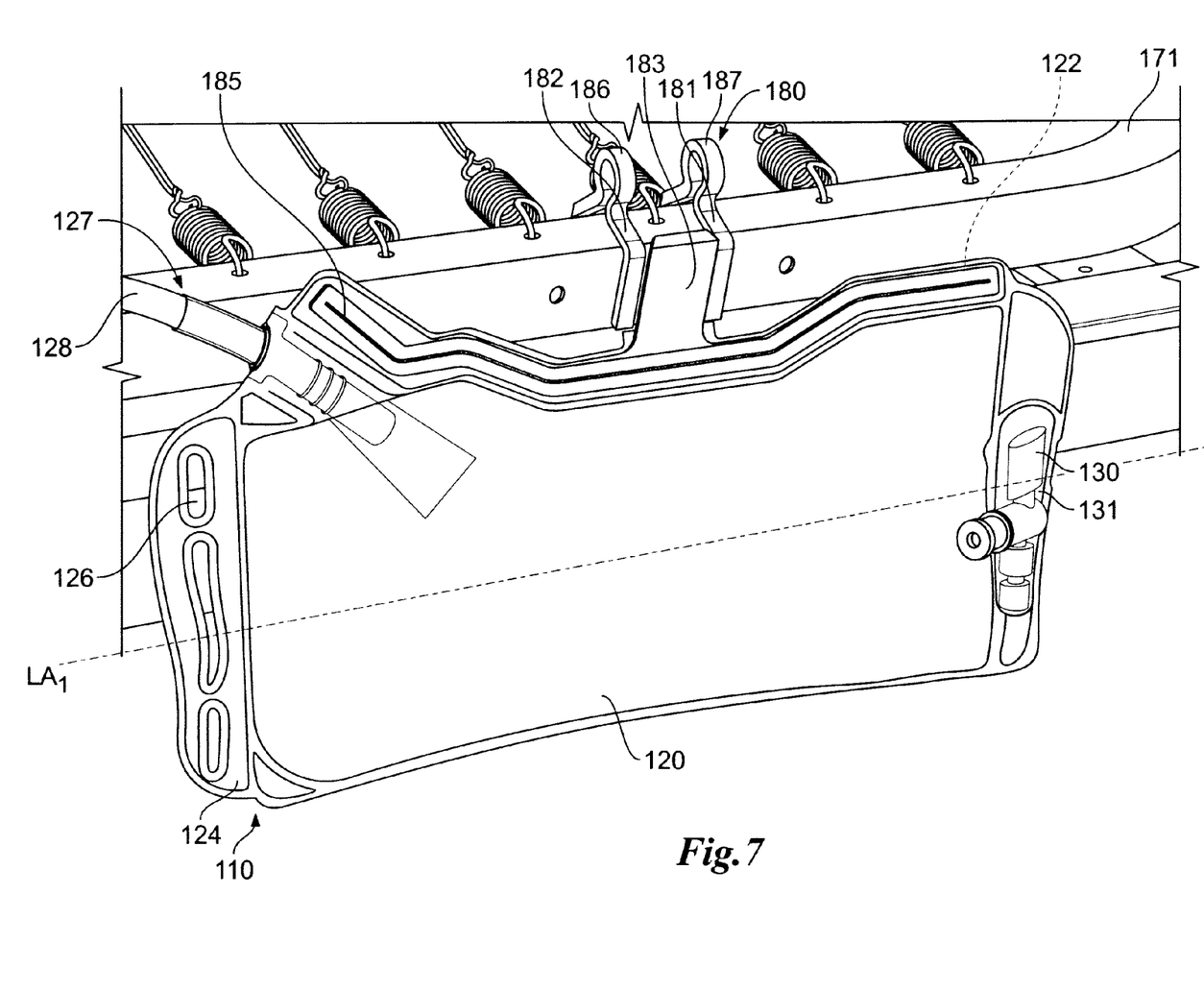
FIG. 7 shows the fluid collection bag of FIGS. 5 and 6 associated with a bed frame.

While the fluid collection bag 110 is shown having a generally rectangular shape, the fluid collection bag 110 may take other polygonal and non-polygonal forms. With any of these shapes, the fluid collection bag 110 includes a first surface 120 and a second surface 122. In the embodiment shown in FIG. 5, the first surface 120 and the second surface 122 are on opposing sides of the fluid collection bag 110 and are bounded on the peripheries by the first side 112, the second side 114, the first end 116 and the second end 118. The first surface 120 and the second surface 122 are generally mirror-images of each other. Furthermore, either the first surface 120 or the second surface 122 may be positioned next to an object or support element, such as a bed frame (as shown in FIG. 7), which allows the fluid collection bag 110 to be reversible. It should be noted that while the fluid collection bag 110 is typically described as being positioned next to and/or secured to a bed or bed frame, in particular a medical bed or bed frame, other non-limiting examples of various types of objects or support elements include patient aids such as a pole, a chair, a wheelchair, a walker, and a person.

To aid in the reversibility of the fluid collection bag 110, the first side 112 includes an attachment member 180 for reversibly attaching the fluid collection bag 110 to an object or support element. By "attaching," it is meant that the attachment member 180 may be adapted to reversibly affix, mount, hang or be manipulated to an object or support element. The attachment member 180 includes a pair of flexible (also referred to as "living") hinges 181, 182, a middle portion 183 separating the flexible hinges 181, 182, and a base portion 184. The flexible hinges 181, 182 are capable of being manipulated from opposing directions to allow the fluid collection bag 110 to be attached with the first surface 120 or the second surface 122 facing the object or support element.

The base portion 184 of the attachment member 180 may be positioned within a top portion of the fluid collection bag 110, as shown in FIG. 5. In some embodiments, the base portion 184 is threaded through the top portion of the fluid collection bag 110 and then the top portion of the fluid collection bag 110 is sealed. In other embodiments, two pieces of plastic film that make up the fluid collection bag 110 may be positioned around the base portion 184 of the attachment member 180 near the top portion of the plastic films and may be sealed or welded, such as by heat or by radio frequency welding, around the base portion 184 to secure the base portion 184 within the top portion of the fluid collection bag 110. The sealing or welding may occur above, below and at the sides of the base portion 184 in a manner that keeps the base portion 184 from sliding back and forth within the top portion of the fluid collection bag 110. This is advantageous because the fluid collection bag 110 remains properly aligned and allows for the center of gravity of the fluid collection bag 110 to be correct. Also, if the fluid collection bag 110 were allowed to slide back and forth within the top portion of the fluid collection bag 110, then the fluid collection bag 110 could tilt and any readings of the volume of the fluid in the fluid collection bag 110 would not be accurate. Thus, it is advantageous to have the base portion 184 held within the top portion of the fluid collection bag 110. Furthermore, having the base portion 184 positioned within the top portion of the fluid collection bag 110 allows the fluid collection bag 110 to be positioned higher off of the floor when it is attached to an object or support element. This allows for easier draining of the fluid collection bag 110 as the fluid collection bag 110 is a farther distance from the floor.

Figure 6:
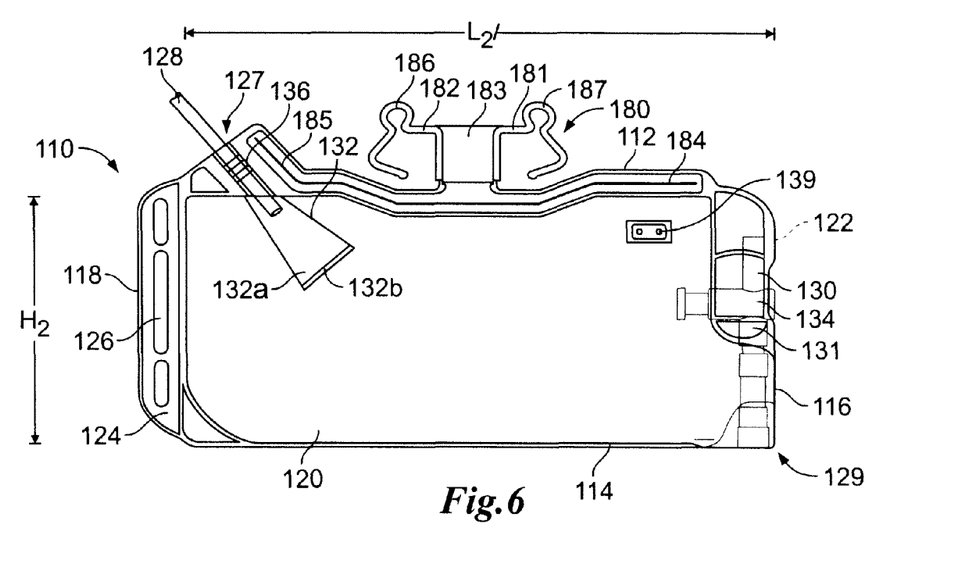

The base portion 184 of the attachment member 180 may be linear or may include angled portions, as shown in FIGS. 5 and 6. The angled portions generally provide improved stability and support for the fluid collection bag 110. In one embodiment, one end of the base portion 184 includes an angled portion 185. The angled portion 185 assists in providing support to the inlet tube 128 to maintain the position of the inlet tube 128 and to keep the inlet opening 127 from sagging or kinking. The angled portions may also allow for an increased volume of fluid that can be held in the fluid collection bag 110, as the angled portions may create a greater height of the fluid collection bag 110. In some embodiments, the angled portions may range from about 10° to about 90°. Typically, the angled portions may be about 10° to about 45°. The base portion 184 can be, for example, a reinforcement rib or bar. Furthermore, the base portion 184 can optionally be in the form of an I-beam that extends along some or the entire length of the fluid collection bag 110 to provide increased strength with less material.

The middle portion 183, the base portion 184 and the flexible hinges 181, 182 of the attachment member 180 may be made of polyolefin, nylon, vinyl, K-Resin®, a styrene-butadiene-copolymer available from Chevron Phillips Chemical in The Woodlands, Tex. as well as other types of plastic that would provide a flexible, "living" hinge. In one non-limiting example, a "living" hinge may be a thin strip molded into a plastic part to create a line along which the part can bend. In other embodiments, it is contemplated that separate hangers (or hinges) made from other types of materials such as metal, wood, and other suitable rigid materials could be used. In yet other embodiments, it is contemplated that some portion(s) of the attachment member 180 could be made of one type of material, such as metal or wood, and other portion(s) could be made of another type of material, such as plastic. Additional details regarding the flexible hinges 181, 182 is provided below in reference to FIGS. 8A-9c.

The flexible hinges 181, 182 are adapted to reversibly affix, mount, hang or be manipulated to an object or support element by flexing, pulling and/or rotating the flexible hinges 181, 182 to place them around the object or support element, such as a bed frame for example. Each of the flexible hinges 181, 182 includes a loop portion 186, 187 that is adapted to be extendable and then spring back into a resting position. The rotation and attachment capability of the flexible hinges 181, 182 is described in more detail below in reference to FIGS. 8A-9C.

As noted earlier, the fluid collection bag 110 is reversible in that it can be affixed, mounted, hung or manipulated to any side of an object or support element. The flexible hinges 181, 182 may be moved from different opposing directions depending on the orientation of the fluid collection bag 110 with respect to the object or support element. For example, the flexible hinges 181, 182 may be flexed, pulled or rotated toward an object or support element and then placed around the object or support element to secure it thereto. Thus, the fluid collection bag 110 can be used and attached to an object or support element with either the first surface 120 or the second surface 122 of the fluid collection bag 110 facing the object or support element. This makes the attaching of the fluid collection bag 110 to an object or support element easier, faster and more convenient.

To describe additional details of the fluid collection bag 110 illustrated in the embodiment shown in FIGS. 5 and 6, the first end 118 may include an end reinforcement 124 having one or more end openings 126. The end openings 126 assist in enabling the fluid collection bag 10 to be handled by a nurse or other handler of the fluid collection bag 110. Additionally, the end openings 126 assist in permitting the fluid collection bag 110 to become associated with and/or affixed to other types of objects or support elements, such as a pole, a chair, a wheelchair, a walker, and a person. The end reinforcement 124 is generally comprised of plastic but can be comprised of woven or non-woven material, molded or stamped material, wood, metal, paperboard, or any rigid or flexible material, as well. The end openings 126 may be generally elliptically-shaped, but may also take other shapes. Furthermore, the end openings 126 are of a size sufficient to facilitate affixing, mounting, hanging or manipulating the fluid collection bag 110. The end openings 126 are generally reinforced for ease of use and durability. Although a total of three end openings 126 are depicted in the embodiment of FIGS. 5 and 6, any number of end openings 126 suitable for assisting in affixing, mounting, hanging or manipulating the fluid collection bag 110 onto an object or support element may be used.

An inlet opening 127, adapted to receive an inlet tube 128, is located along the first side 112 of the fluid collection bag 110. An outlet opening 129, adapted to receive an outlet tube 130, is located along the second side 114 of the fluid collection bag 110. However, it is contemplated that the fluid collection bag 110 may have additional inlet and outlet openings and tubes. Additionally, the inlet and outlet openings 127, 129 may be located in other positions on the fluid collection bag 110 than those illustrated in the figures. Before use of the fluid collection bag 110, the inlet tube 128 is associated with the fluid collection bag 110 at the inlet opening 127 at one end. The exposed end of the inlet tube 128 is typically connected to a catheter (not illustrated). The outlet tube 130 is associated with the fluid collection bag 110 at the outlet opening 129 at one end. The exposed end of the outlet tube 130 may be inserted into a drain tube holder 131, which is discussed in more detail below.

In the illustrated embodiment, the inlet tube 128 associates with the fluid collection bag 110 at an angle to reduce twisting and to allow for good drainage. In one embodiment, the inlet tube 128 may associate with the fluid collection bag 110 at an angle within the range of about 30° to about 50°. However, it is contemplated that any angle which is suitable for reducing twisting and allowing good drainage for the inlet tube 128 may be used.

Near the inlet opening 127 and internal to the fluid collection bag 10 is an anti-reflux mechanism 132. The anti-reflux mechanism 132 is adapted to generally surround the inlet tube 128 and comprises two sheets 132a, 132b having different lengths in the embodiment shown in FIG. 5. The anti-reflux mechanism 132 may be comprised of vinyl; however, other materials are contemplated for use. Some non-limiting examples of materials for use in the anti-reflux mechanism 132 include plastic film, molded plastic, and rubber. At one end, at least one sheet, i.e., 132a or 132b, of the anti-reflux mechanism 132 may be associated with the fluid collection bag 110 at or near the inlet opening 127 or the inlet tube 128 itself. The other end of the anti-reflux mechanism 132 is free. The anti-reflux mechanism 132 assists in allowing fluid to enter the fluid collection bag 110 while inhibiting fluid from exiting the fluid collection bag 110 through the inlet tube 128. To inhibit fluid from exiting through the inlet tube 128, the sheets 132a, 132b collapse and assist in sealing the end of the inlet tube 128 internal to the fluid collection bag 110 when fluid attempts to exit through the inlet tube 128. It should be noted that other types of anti-reflux mechanisms having different designs and/or different numbers of sheets may also be used.

A user may control the exit of fluid from the fluid collection bag 110 through the outlet tube 130 using a valve 134. The valve 134 may be any of those types of valves which are adapted to open or close a fluid path to allow fluid to drain or keep fluid from draining. In one embodiment, the valve 134 is adapted to replace a drainage hole with a post when activated. In other embodiments, the valve 134 may, for example, be a twist valve, a tube that closes with a mechanical compression against it, or a roller clamp. Additionally, in some embodiments, more than one valve may be utilized.

As shown in FIG. 6, the outlet tube 130 may be adapted to be stored in the drain tube holder 131. The drain tube holder 131 may be positioned near or adjacent to the first end 116 and may include a pocket, notch, opening, slit, tubing, or molded piece that easily stores the outlet tube 130. Additionally, the drain tub holder 131 may be puckered or may include a puckered area such that the drain tube holder 131 remains in an open position without requiring it to be manually opened by a user of the fluid collection bag 110. In some embodiments, the outlet tube 130 may be stored while the fluid collection bag 110 is oriented with the first surface 120 or the second surface 122 facing the object or support element. For example, the outlet tube 130 may be swung from its hanging position in FIG. 5 into the drain tube holder 131 from either direction relative to the first surface 120 or the second surface 122. This allows the fluid collection bag 110 to be able to be attached to an object or support element with either the first surface 120 or the second surface 122 of the fluid collection bag 110 facing the object or support element. As with the other reversible features, this makes the use of the fluid collection bag 110 easier and more convenient for a user. For example, as it is important that the inlet tube 128 face toward the head of a bed to achieve unobstructed flow, the reversibility of the fluid collection bag 110 insures that the inlet tube 128 may always be facing in a desirable orientation. In non-reversible bags, for the inlet tube 128 to face toward the head of the bed, the fluid collection bag 110 must be positioned on one side or the other. This limits the ease of use and convenience of such non-reversible bags and, thus, a fluid collection bag 110 that is reversible is particularly desirable. Thus, the reversibility of the fluid collection bag 110 is in part due to (1) the ability of the attachment member 180 to attach to an object or support element while the fluid collection bag 110 is oriented with the first surface 120 or the second surface 122 facing the object or support element and (2) the ability of the outlet tube 130 to be stored in the drain tube holder 131 while the fluid collection bag 110 is oriented with the first surface 120 or the second surface 122 facing the object or support element. This reversibility of the fluid collection bag 110 has several advantages in that it offers increased ease, convenience and speed in attaching the fluid collection bag 110 to an object or support element, such as a bed frame.

Additionally, the inlet tube 128 and the outlet tube 130 may include one or more ribs 136 to discourage kinking or compression within the inlet and outlet tubes 128, 130. The ribs 136 enable good flow through the inlet and outlet tubes 128, 130 and allow for good drainage of the fluid collection bag 110. The fluid collection bag 110 may also include a vent 139. The vent 139 may include a hydrophilic air vent allowing air transfer to inhibit pressure effects such as a vacuum effect in the fluid collection bag 110. The fluid collection bag 110 may also include a printed window (not shown) on either the first surface 120, the second surface 122 or both the first surface 120 and the second surface 120 of the fluid collection bag 110. The printed window(s) may include measurement line(s) to enable easy urine volume output determination.

Referring now to FIG. 7, the fluid collection bag 110 is shown in use, i.e., attached to a bed frame 171, according to one embodiment of the present concepts. Generally, the attachment member 180 is adapted to removably and reversibly associate with an object or support element, such as a bed frame. More specifically, the flexible hinges 181, 182 of the attachment member 180 are adapted to contact a bed frame 171 wherein the flexible hinges 181, 182 are positioned around the bed frame 171. The flexible hinges 181, 182 grip the portions of the bed frame 171 and allow it to be secured thereto. The middle portion 183 may contact the side of the bed frame 171. The loop portions 186, 187 of each of the flexible hinges 181, 182 are extendable around the bed frame 171 and adapted to spring back into a resting position. The shape and flexible nature of the flexible hinges 181, 182 enable the fluid collection bag 110 to removably and reversibly attach to different types of objects and support elements and different desired end uses. For example, the flexible hinges 181, 182 may grip different shapes of objects, such as rounded objects, rectangular objects, L-shaped objects, etc. In particular, the flexible hinges 181, 182 can conform to all shapes and sizes of bed frames, wheelchairs, and other objects and support elements. In some embodiments, the one or more end openings may also be used to assist in attaching the fluid collection bag 110 to an object or support element, such as a bed frame. Additionally, a cord, tape or other suitable attaching material may be used to assist in attaching the fluid collection bag 110 to the object or support element.

In FIG. 7, the inlet tube 128 is shown as extending from the inlet opening 127 of the fluid collection bag 110. The angled portion 185 assists in maintaining the inlet tube 128 in an optimal position for fluid flow through the inlet tube 128. The outlet tube 130 is shown as being stored within the drain tube holder 131. This assists in preventing the outlet tube 130 from being contaminated. As noted above, the ability of the outlet tube 130 to be stored in the drain tube holder 131 regardless of whether the first surface 120 or the second surface 122 of the fluid collection bag 110 faces the object or support element permits use of the fluid collection bag 110 in an easier, more convenient and an improved manner over existing fluid collection bags.

As illustrated, the longitudinal axis $LA_1$ of the fluid collection bag 110 is oriented substantially parallel to the ground. When a bed is in a low position, the fluid collection bag 110 does not contact the ground and the outlet tube 130 remains generally away from the ground, inhibiting the potential for contamination and/or spread of infection. As the outlet tube 130 is positioned in the tube holder 131 as shown in FIG. 6, this also prevents or inhibits the potential for contamination and/or spread of infection.

As mentioned above, the end openings 126 on the end reinforcement 124 are provided to enable attachment of the fluid collection bag 110 to objects or support elements in addition to beds. Such additional objects or support elements include, but are not limited to, patient aids such as a pole, a chair, a wheelchair, a walker, and person. In some embodiments, other methods of affixing, mounting, hanging or otherwise manipulating the fluid collection bag 110 onto the desired object or support element may include the use of securement materials such as tape, Velcro® or other hook and loop type fastening devices. In other embodiments, the securement material for affixing, mounting, hanging or otherwise manipulating the fluid collection bag 110 onto the desired object or support element may include snaps, cords, buttons, or other fastening devices.

To use the fluid collection bag 110, a user would associate the attachment member 180, particularly the flexible hinges 181, 182, to an object or support element, such as a bed frame, as illustrated in FIG. 7. The user would then orient the longitudinal axis $LA_1$ of the fluid collection bag 110 substantially parallel to the ground and removably and reversibly associate the fluid collection bag 110 with the object or support element, such as a bed frame 171. Although FIG. 7 illustrates an example in which the end openings 126 are not utilized to attach the fluid collection bag 110 to an object or support element, other embodiments are contemplated wherein the end openings 126 assist in attaching the fluid collection bag 110 to an object or support element.

Figure 8A:
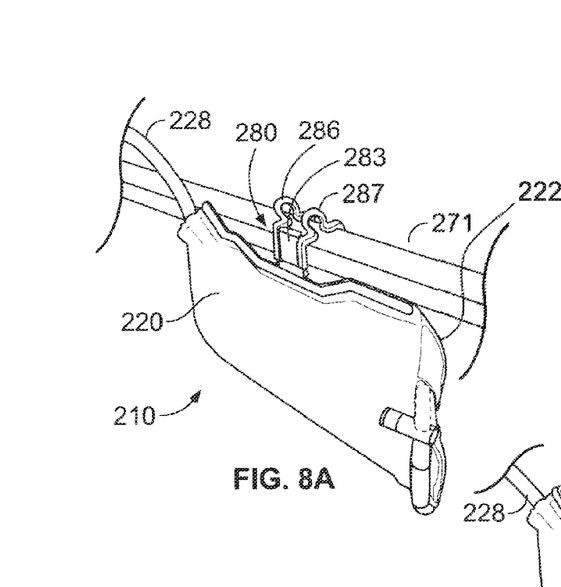
FIG. 8A is a perspective view illustrating a fluid collection bag according to yet another embodiment.
Figure 8B:
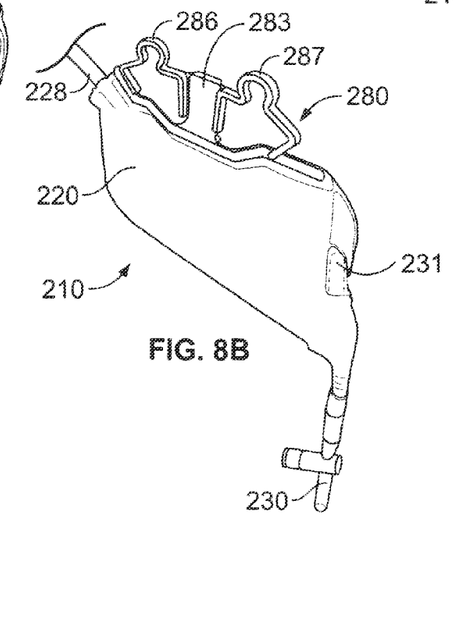
FIG. 8B is a perspective view illustrating the fluid collection bag of FIG. 8B having a pair of flexible hinges and an outlet tube in respective intermediate positions.
Figure 8C:
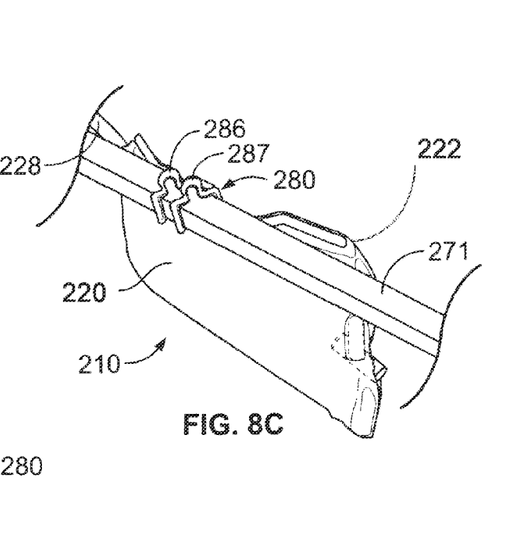
FIG. 8C is a perspective view illustrating the fluid collection bag of FIG. 8A in a reversed position.

Referring to FIGS. 8A-8C, a fluid collection bag 210 includes a first surface 220, a second surface 222, an inlet tube 228, an outlet tube 230, and an attachment member 280. In general, the fluid collection bag 210 is similar (but not necessarily identical) to the fluid collection bag 110 described above. The attachment member 280 has a middle portion 283 that is coupled to a pair of loop portions 286, 287 for attaching to a bed frame 271 or other objects or support elements.

The loop portions 286, 287 are rotatable around the middle portion 283 for reversibly attaching the fluid collection bag 210 to either side of the bed frame 271. For example, in a first attachment position (illustrated in FIG. 8A) the loop portions 286, 287 are oriented perpendicular to the middle portion 283 and away from the first surface 220. In the first attachment position the first surface 220 is positioned to face away from the bed frame 271, while the second surface 222 is positioned to face toward the bed frame 271.

To reverse the fluid collection bag 210, the loop portions 286, 287 are rotated 180°, through one or more intermediate positions (e.g., FIG. 8B), until reaching a second attachment position (illustrated in FIG. 8C). The exemplary intermediate position illustrated in FIG. 8B has the loop portions 286, 287 rotated about 90° relative to the first attachment position, the loop portions 286, 287 being generally parallel to the middle portion 283. In the second attachment position, the second surface 222 is positioned to face away from the bed frame 271 and the first surface 220 is positioned to face toward the bed frame 271.

When reversing the fluid collection bag 210, the outlet tube 230 is also reversed from the first surface 220 to the second surface 222. The reversal of the outlet tube 230 is described in more detail below in reference to FIGS. 10A-10E.

Figure 9A:
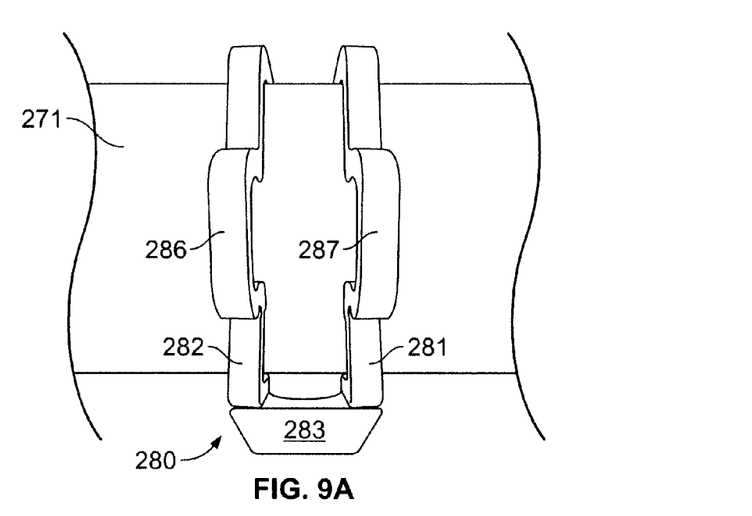
FIG. 9A is a top view illustrating an attachment member of the fluid collection bag of FIG. 8A in an initial position.
Figure 9B:
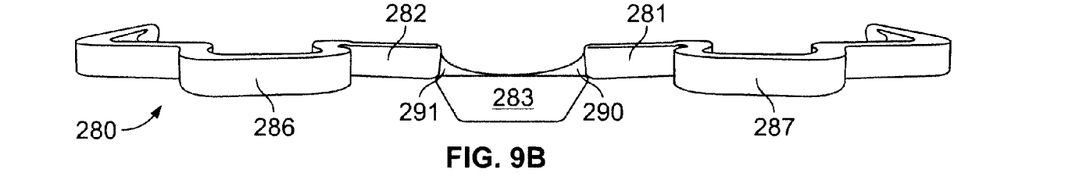
FIG. 9B is a top view illustrating the attachment member of FIG. 9A in an intermediate position.
Figure 9C:
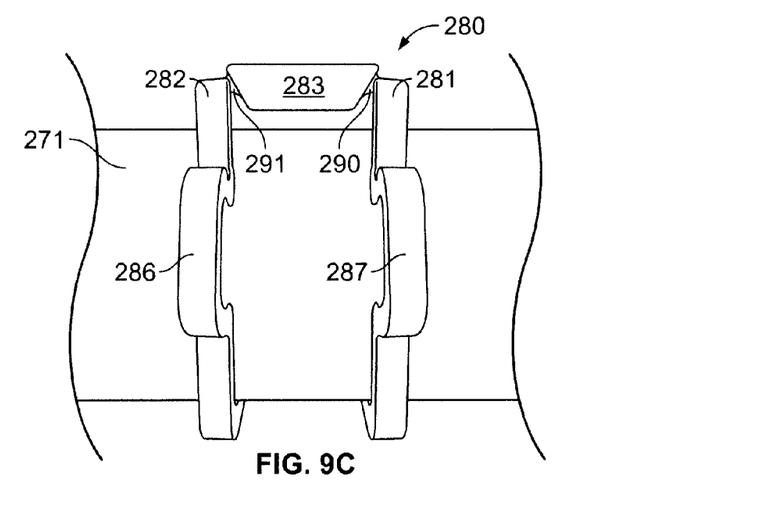
FIG. 9C is a top view illustrating the attachment member of FIG. 9A in a reversed position.
Figure 10A:
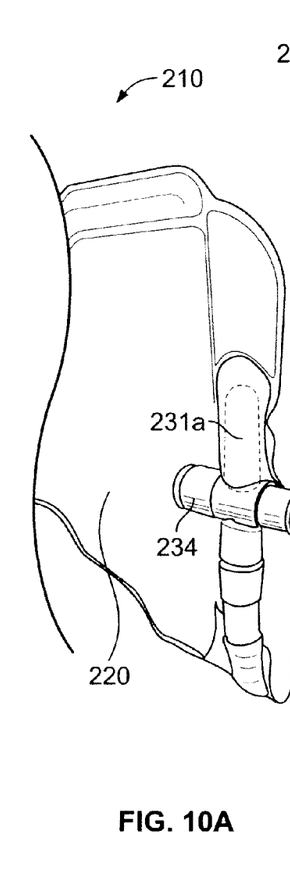
FIG. 10A is a partial perspective view of the fluid collection bag of FIG. 8A illustrating the outlet tube in the initial position.
Figures 10B, 10C:
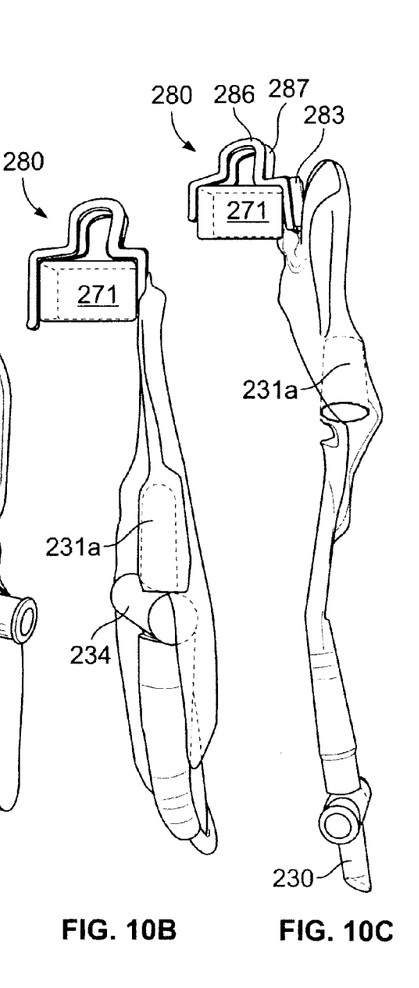
FIG. 10B is an end view of the fluid collection bag of FIG. 8A illustrating the outlet tube in the initial position.
FIG. 10C is an end view of the fluid collection bag of FIG. 8A illustrating the outlet tube in the intermediate position.
Figure 10D:
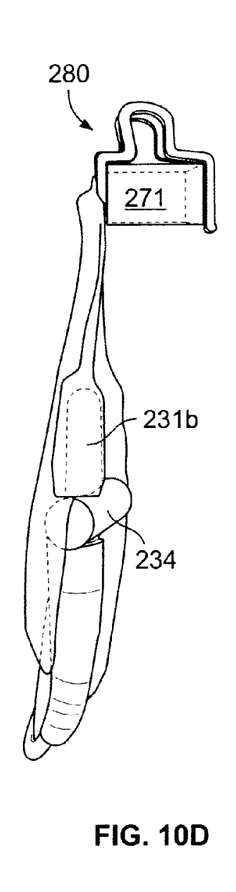
FIG. 10D is an end view of the fluid collection bag of FIG. 8A illustrating the outlet tube in the reversed position
Figure 10E:
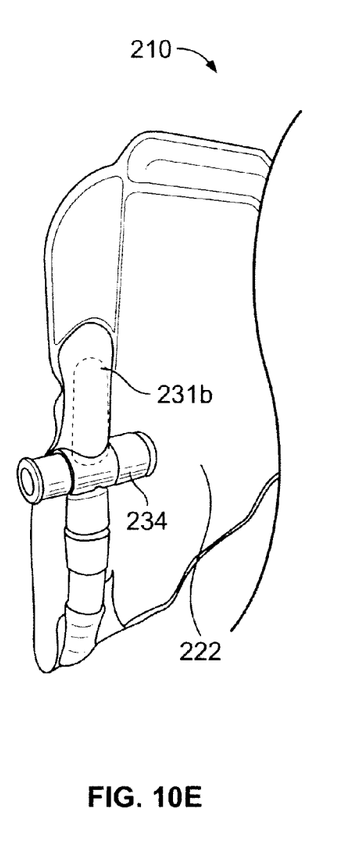
FIG. 10E is a partial perspective view of the fluid collection bag of FIG. 8A illustrating the outlet tube in the reversed position.

Referring to FIGS. 9A-9C, the attachment member 280 is shown more clearly to illustrate a pair of living hinges 281, 282 for coupling the loop portions 286, 287 to the middle portion 283. Optionally, the attachment member 280 can be a single unitary molded component. Furthermore, the living hinges 281, 282 are attached to the middle portion 283 via a pair of flexible portions 290, 291. When the attachment member 280 is in the first attachment position (illustrated in FIG. 9A), the flexible portions 290, 291 are generally compressed between the living hinges 281, 282 and the middle portion 283. When the attachment member 280 is in the intermediate position (illustrated in FIG. 9B), the flexible portions 290, 291 are partially stretched to allow the rotational movement of the loop portions 286, 287. When the attachment member 280 is in the second attachment position (illustrated in FIG. 9C), the flexible portions 280, 291 are generally fully stretched to allow the 180° position reversal of the loop portions 286, 287. The flexible portions 290, 291 can be thinned portions to permit easy bendability with respect to the middle portion 283.

Referring to FIGS. 10A-10E, the outlet tube 230 is also reversed when reversing attachment of the fluid collection bag 210 from one side of the bed frame 271 to another side of the bed frame 271. Reversal of the outlet tube 230 provides easy access to a user, regardless of which one of the first and second surfaces 220, 222 is facing toward the bed frame 271.

In the first attachment position (illustrated in FIGS. 10A-10B), the outlet tube 230 is inserted inside a first drain tube holder 231a, which is located on the first surface 220 of the fluid collection bag 210. In this position, a valve 234 is located adjacent to the first drain tube holder 231a.

When reversing the fluid collection bag 210, the outlet tube 230 is removed from the first drain tube holder 231a and is rotated through a plurality of intermediate positions. For example, the outlet tube 230 is rotated about 90° downward in an exemplary intermediate position (illustrated in FIG. 10C). In this intermediate position, the outlet tube 230 reaches its maximum extension away from the fluid collection bag 210. To complete the reversibility of the outlet tube 230, the outlet tube is rotated to the second attachment position (illustrated in FIGS. 10D-10E) in which the outlet tube 230 is inserted in a second drain tube holder 231b, which is located on the second surface 222 of the fluid collection bag 210.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A method of securing a reversible fluid collection bag to a support element, comprising:
    orienting a longitudinal axis of the reversible fluid collection bag substantially parallel to the ground, the reversible fluid collection bag including:
        an inlet opening adapted to receive an inlet tube located on a first side of the fluid collection bag,
        an outlet opening adapted to receive an outlet tube located on a second side of the fluid collection bag, the second side being generally parallel with the first side of the fluid collection bag,
        a first surface extending from the first side to the second side,
        a second surface extending from the first side to the second side, the second surface opposing the first surface, and
        a tube holder adapted to store the outlet tube on the first surface of the fluid collection bag while the fluid collection bag is oriented with the opposing second surface of the fluid collection bag facing the support element and to store the outlet tube on the second surface while the fluid collection bag is oriented with the first surface facing the support element such that the fluid collection bag is reversible with respect to the support element; and
    attaching the reversible fluid collection bag to the support element via an attachment member, the attachment member including flexible hinges for engaging the support element, the flexible hinges capable of rotating in opposing directions to engage the support element such that the reversible fluid collection bag can be attached from the first surface or the second opposing surface.

2. The method of claim 1, further comprising rotating the outlet tube about the second side of the fluid collection to move the outlet tube from a first position to a second position, the outlet tube being stored by the tube holder on the first surface in the first position, the outlet tube being stored by the tube holder on the second surface in the second position.

3. The method of claim 1, the tube holder includes a tubing to store the outlet tube.

4. The method of claim 1, wherein the tube holder includes a slit.

5. The method of claim 1, wherein the tube holder includes a puckered area such that the tube holder remains in an open position.

6. A method of securing a reversible fluid collection bag to a support element, the reversible fluid collection bag including an inlet opening adapted to receive an inlet tube located on a first side of the fluid collection bag, an outlet opening adapted to receive an outlet tube located on a second side of the fluid collection bag, the second side being generally parallel with the first side of the fluid collection bag, a first surface extending from the first side to the second side, a second surface extending from the first side to the second side, the second surface opposing the first surface, the method comprising:
    attaching the fluid collection bag to the support element with the first surface of the fluid collection bag facing the support element;
    storing the outlet tube on the opposing second surface of the fluid collection bag in a tube holder;
    detaching the fluid collection bag from the support element and reversing the orientation of the fluid collection bag relative to the support element;
    attaching the fluid collection bag to the support element with the opposing second surface of the fluid collection bag facing the support element; and
    storing the outlet tube on the first surface of the fluid collection bag in the tube holder.

7. The method of claim 6, wherein the reversible fluid collection bag further includes an attachment member including flexible hinges for engaging a support element, the flexible hinges capable of moving in opposing directions to engage the support element such that the fluid collection bag can be reversibly attached while the fluid collection bag is oriented with the first surface or the second opposing surface facing a support element, the flexible hinges extending from the fluid collection bag in a direction generally from the first surface to the second surface when the fluid collection bag is attached to the support element with the second surface facing the support element, the flexible hinges extending from the fluid collection bag in a direction generally from the second surface to the first surface when the fluid collection bag is attached to the support element with the first surface facing the support element.

8. The method of claim 7, further comprising, in response to the detaching and reversing, moving the flexible hinges from a first position to a second position, the flexible hinges extending from the fluid collection bag in a direction generally from the second surface to the first surface in the first position, the flexible hinges extending from the fluid collection bag in a direction generally from the first surface to the second surface in the second position.

9. The method of claim 6, wherein the storing the outlet tube on the first surface comprises rotating the outlet tube about the second side of the fluid collection to move the outlet tube from a position on the first surface to a position on the second surface.

10. The method of claim 6, wherein the tube holder includes a slit.

11. The method of claim 6, wherein the tube holder includes a puckered area such that the tube holder remains in an open position.

12. The method of claim 6, wherein the tube holder includes a tubing to store the outlet tube.

* * * * *